(12) United States Patent
Nuckley et al.

(10) Patent No.: US 9,084,635 B2
(45) Date of Patent: Jul. 21, 2015

(54) INTRAOPERATIVE SPINAL STABILIZATION

(71) Applicant: Regents of the University of Minnesota, St. Paul, MN (US)

(72) Inventors: David John Nuckley, Minneapolis, MN (US); David Wayne Polly, Jr., Edina, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 218 days.

(21) Appl. No.: 13/646,353

(22) Filed: Oct. 5, 2012

(65) Prior Publication Data

US 2013/0090692 A1    Apr. 11, 2013

Related U.S. Application Data

(60) Provisional application No. 61/544,908, filed on Oct. 7, 2011.

(51) Int. Cl.
*A61B 17/70*     (2006.01)
*A61B 17/68*     (2006.01)
*A61B 19/00*     (2006.01)

(52) U.S. Cl.
CPC ......... *A61B 17/7047* (2013.01); *A61B 17/7068* (2013.01); *A61B 2017/681* (2013.01); *A61B 2019/5287* (2013.01); *A61B 2019/5483* (2013.01)

(58) Field of Classification Search
CPC .......... A61B 17/7047; A61B 17/7068; A61B 2017/681
USPC ......................................... 606/246, 277, 278
See application file for complete search history.

(56) References Cited

U.S. PATENT DOCUMENTS

| | | | | |
|---|---|---|---|---|
| 3,693,616 | A * | 9/1972 | Roaf et al. | 606/250 |
| 4,078,559 | A * | 3/1978 | Nissinen | 606/258 |
| 4,573,454 | A * | 3/1986 | Hoffman | 606/250 |
| 4,604,995 | A * | 8/1986 | Stephens et al. | 606/261 |
| 4,773,402 | A * | 9/1988 | Asher et al. | 606/250 |
| 5,413,576 | A * | 5/1995 | Rivard | 606/250 |
| 6,000,399 | A | 12/1999 | Choy | |
| 6,224,597 | B1 | 5/2001 | Coker | |
| 6,324,710 | B1 | 12/2001 | Hernandez et al. | |
| 7,832,906 | B2 * | 11/2010 | Damman | 362/311.13 |
| 8,435,268 | B2 * | 5/2013 | Thompson et al. | 606/279 |
| 2005/0059972 | A1 * | 3/2005 | Biscup | 606/73 |
| 2008/0021466 | A1 * | 1/2008 | Shadduck et al. | 606/61 |
| 2008/0177326 | A1 * | 7/2008 | Thompson | 606/277 |

* cited by examiner

*Primary Examiner* — Ellen C Hammond
(74) *Attorney, Agent, or Firm* — Shumaker & Seiffert, P.A.

(57) ABSTRACT

A number of spinal stabilization devices are disclosed for aligning and fixing vertebrae during surgery, e.g. to facilitate accurate placement of pedicle screws. One stabilization device includes a pair of spiked rails biased to clamp shut and thereby passively engage a number of vertebrae. Another stabilization device includes a tie-rod that connects two or more fiducial markers, each of which is connected to a vertebra, to stabilize the vertebrae including and between each vertebra to which the markers are attached.

27 Claims, 4 Drawing Sheets

INTRAOPERATIVE SPINAL STABILIZATION

This application claims the benefit of application No. 61/544,908, filed Oct. 7, 2011, the entire content of which is incorporated herein by reference.

TECHNICAL FIELD

This disclosure relates to tools and methods employed during spinal surgery.

BACKGROUND

Of the many spinal surgeries performed in the United States each year, pedicle screw fixation is one of the more common surgical techniques used to stabilize the spine for patients with spinal fracture, and degenerative or scoliotic deformities. The effectiveness of pedicle screws is dependent, at least in part, upon the accuracy of their placement. In spite of their effectiveness in the cervical spine, the use of pedicle screws is limited due to the difficulty in placing the screws. The difficulty in placing the screws is accentuated by the flexibility of the cervical spine. In particular, as force is applied to a vertebra to insert a screw, the vertebra may move, altering the trajectory of the screw.

SUMMARY

In general, the following examples are directed to tools and methods for aligning and fixing vertebrae during surgery to facilitate accurate placement of pedicle screws. The spinal stabilization techniques described below may improve the use of pedicle screws due to the increased accuracy of the placement of the screws and may also reduce screw revision rates and improve outcomes, both of which may lead to improved efficacy at lower costs.

In one example, a spinal stabilization device includes a clamp, a first rail, and a second rail. The clamp is configured to engage a vertebra of a spine. The first rail is connected to the clamp and includes a number of spikes distributed longitudinally along the first rail. The second rail is connected to the clamp offset laterally from the first rail and includes a number of spikes distributed longitudinally along the second rail. The first rail and the second rail are biased toward one another with the first plurality of spikes pointing toward the second plurality of spikes.

In another example, a kit includes a plurality of spinal stabilization devices. Each spinal stabilization device includes a clamp, a first rail, and a second rail. The clamp is configured to engage a vertebra of a spine. The first rail is connected to the clamp and includes a first plurality of spikes distributed longitudinally along the first rail. The second rail is connected to the clamp offset laterally from the first rail and includes a second plurality of spikes distributed longitudinally along the second rail. The first rail and the second rail are biased toward one another with the first plurality of spikes pointing toward the second plurality of spikes. The plurality of spinal stabilization devices include a variety of offsets between the first rail and the second rail in a range from approximately 7 to approximately 15 millimeters.

In another example, a spinal stabilization device includes a first fiducial marker to engage a first vertebra of a spine, a second fiducial marker to engage a second vertebra of the spine, and a tie-rod rigidly affixed between the first and second fiducial markers to stabilize the spine.

In another example, a kit includes a plurality of spinal stabilization devices. Each of the spinal stabilization devices includes a first fiducial marker to connect to a first vertebra, a second fiducial marker to connect to a second vertebra, and a tie-rod connected to the first and second fiducial markers. The plurality of spinal stabilization devices include a plurality of tie-rods of a plurality of different lengths.

The details of one or more examples are set forth in the accompanying drawings and the description below. Other features, objects, and advantages of examples according to this disclosure will be apparent from the description and drawings, and from the claims.

DETAILED DESCRIPTION

Placement of screws into the human spine is a common surgical procedure to allow for a multitude of spinal surgeries to be performed. Pedicle screws, as they are commonly referred to are typically placed into the pedicles of individual vertebra in different regions of the spine, including the cervical, lumbar, and sacral spine. The pedicle screws are driven into a vertebra by a surgeon, typically using a manual driver. The orientation of each screw with respect to the vertebra into which the screw is driven, as well as the spinal column as a whole is an important characteristic of proper pedicle screw placement. However, as force is applied to a vertebra to insert a screw, the vertebra and other adjacent vertebrae may move, altering the trajectory of the screw and the orientation of the screw with respect to the patient's spine. Thus, the following examples are directed to tools and methods for aligning and fixing vertebrae during surgery to facilitate accurate placement of pedicle screws. The spinal stabilization techniques described below may improve the use of pedicle screws by improving placement accuracy.

In one example, two spiked rails are employed to form jaws that clamp and stabilize multiple vertebrae along the length of a spine. The rails are biased toward the longitudinal axis of the spinal column such that no active fixation element is required to attach the rails to the vertebrae of the spine. To place the spiked rail stabilizer, a surgeon attaches a clamp that is connected to one end of each rail and to a vertebra of the patient. The surgeon then spreads the biased rails, deflecting the rails outward away from the spinal column to allow the rails to be placed over the vertebrae, e.g. over the spinous processes of the vertebrae. After the rails are aligned properly with the vertebrae of the patient, the surgeon may allow the rails to clamp shut, deflecting back toward the spinal column and driving the spikes arranged along the length of each rail into the vertebrae, e.g. into the spinous processes of the vertebrae.

In another example, a tie-rod is rigidly affixed between the shafts of two fiducial markers, each of which is connected to a vertebra of a patient. Tying the fiducial markers to one another with the tie-rod acts to form a stabilizer that aligns and fixes the vertebrae including and between the two vertebra to which the markers are connected.

Figure 1A:
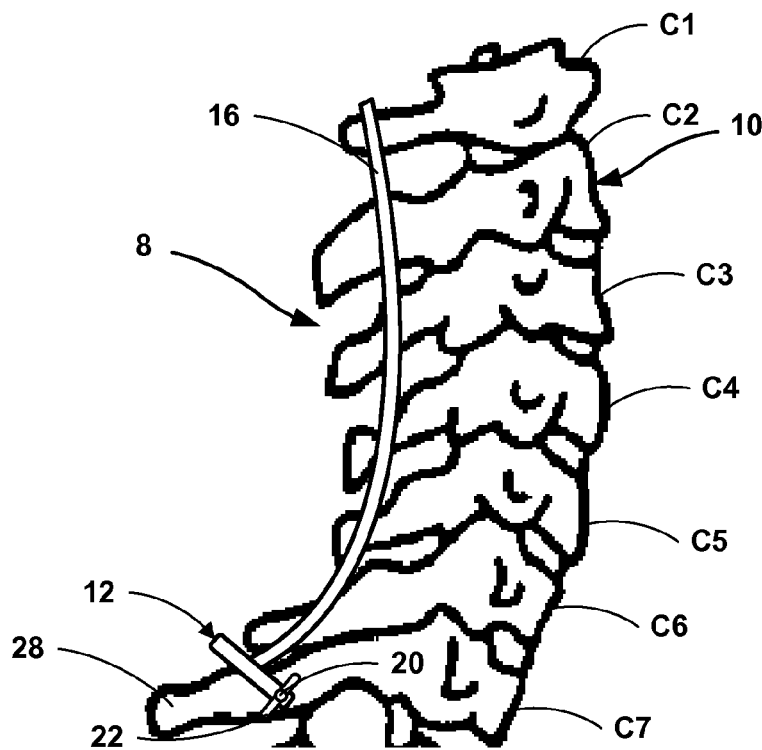
FIGS. 1A and 1B are schematic illustrations of an example spinal stabilization device attached to cervical vertebrae.
Figure 1B:
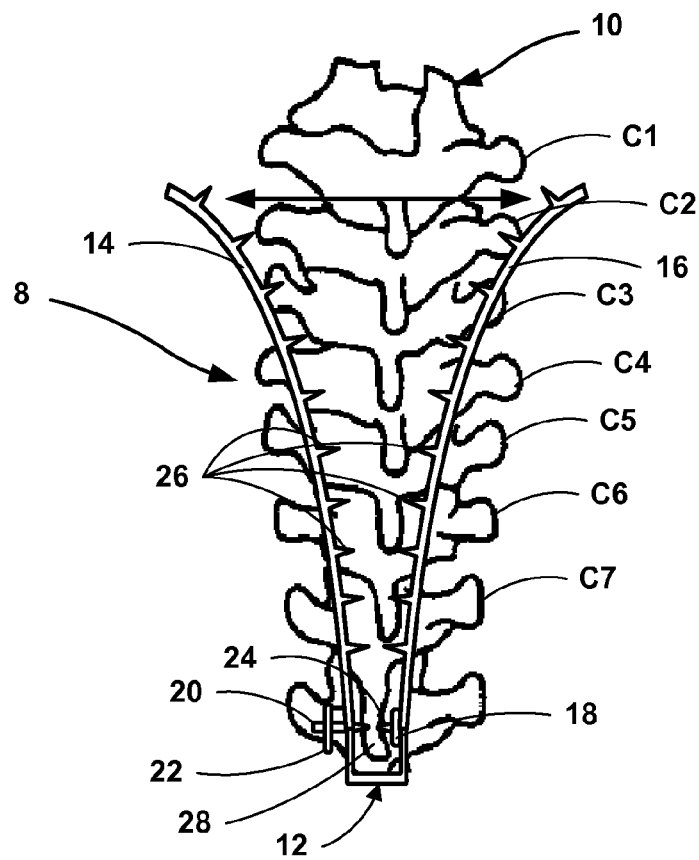

FIGS. 1A and 1B are schematic illustrations of example spiked rail spinal stabilization device 8 arranged to be attached to cervical vertebrae, C1-C7, of spine 10. Spiked rail stabilization device 8 includes base clamp 12, first rail 14, and second rail 16. Clamp 12 includes a c-clamp including fixed jaw 18 and adjustable screw 20, which is driven by handle 22. Fixed jaw 18 may include a number of spikes that may be driven into spinal bone of a vertebra, including, e.g. spike 24 illustrated in the example of FIGS. 1A and 1B. Each of first rail 14 and second rail 16 includes a number of spikes 26 distributed along the length of the rails. One end of each of first rail 14 and second rail 16 is connected to clamp 12 such that the rails extend from the clamp longitudinally along spine 10.

Clamp 12 and first and second rails 14 and 16, respectively, may be manufactured from a variety of materials, including metals such as steel, nickel, cobalt-chromium and aluminum or various polymers and carbon reinforced polymers. In some examples, clamp 12 and rails 14 and 16 may be manufactured from a number of biocompatible materials that resist corrosion and degradation from bodily fluids including, e.g., titanium or stainless steel, or a biologically inert polymer. Additionally, first and second rails 14 and 16, respectively, may be manufactured from a shape memory alloy, including, e.g., a nickel-titanium alloy such as Nitinol.

First rail 14 and second rail 16 may be connected to clamp 12 in a number of ways, including by welding, brazing, gluing, or otherwise adhering the rails to the clamp. In another example, first and second rails 14 and 16 are removably attached to clamp 12, e.g., by fastening each rail to the clamp. Rails 14 and 16 are manufactured from an elastic material and are biased into a generally straight shape such that, when connected to clamp 12, the rails will clamp shut toward one another when not subjected to an external force. The spring constant of each of first rail 14 and second rail 16 may be such that a force in a range from approximately 50 to approximately 150 newtons is required to overcome the inherent biasing of the rails and deflect them, e.g. spread them away from one another and away from cervical vertebrae C1-C7 as illustrated in FIG. 1B.

In the example of FIGS. 1A and 1B, a surgeon may place spiked rail stabilizer 8 on spine 10 by attaching clamp 12 to cervical vertebra C7 of the patient. Clamp 12 may be attached to C7 by turning handle 22 to open screw 20 such that the distance between screw 20 and spike 24 protruding from fixed jaw 18 is sufficient to arrange the clamp around spinous process 28 of vertebra C7. After clamp 12 is placed over spinous process 28 of vertebra C7, the surgeon may engage the clamp by driving screw 20 into the vertebra using handle 22. When attached to vertebra C7, the tip of screw 20 and spike 24 protruding from fixed jaw 18 may penetrate into spinous process 28. As illustrated in FIG. 1B, after clamp 12 is attached to vertebra C7, the surgeon spreads biased first and second rails 14 and 16 to deflect the rails outward away from spine 10 to allow the rails to be placed over the C1-C6 vertebrae, e.g. over the spinous processes of the vertebrae. As illustrated in FIG. 1A, one or both of rails 14 and 16 may be contoured to follow the curvature of spine 10. After first and second rails 14 and 16 are aligned properly with vertebrae C1-C6 of the patient, the surgeon may allow the rails to clamp shut, deflecting back toward the spinal column and driving spikes 26 arranged along the length of each rail into the vertebrae, e.g. into the spinous processes of the vertebrae.

In one example, first and second rails 14 and 16, respectively, may be fabricated from a shape memory alloy, e.g. Nitinol, which may function to bias the rails to spread apart to be positioned in cooler temperatures, e.g. room temperatures or cooler outside of the body and then bias the rails to clamp shut toward the spinal column in warmer temperatures, e.g. near body temperatures when placed over the spine of a patient.

Figure 2:
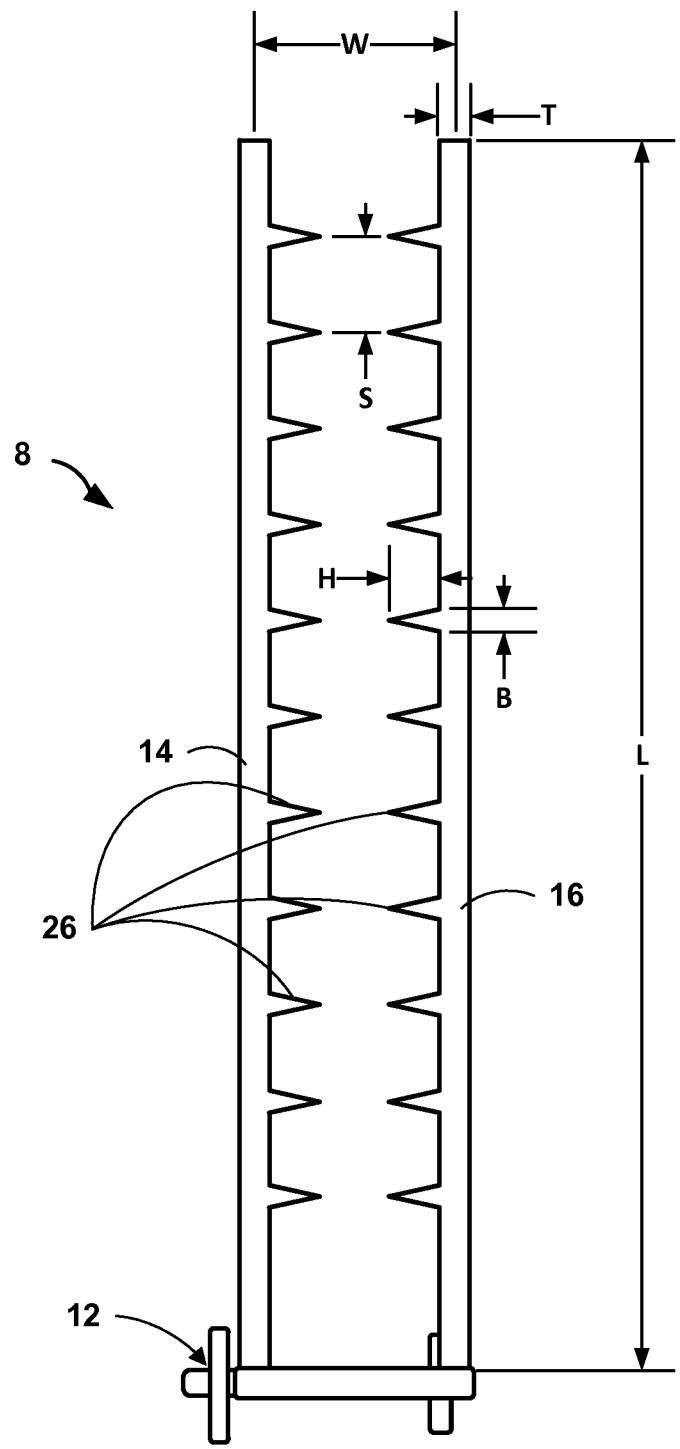
FIG. 2 is a plan view of the spinal stabilization device of FIGS. 1A and 1B.

FIG. 2 is a plan view of spiked rail spinal stabilization device 8 of FIGS. 1A and 1B illustrating the relative size of the device, including the length, L, of rails 14 and 16, the center-to-center width, W, between the rails, the thickness (e.g. diameter), T, of each of rail, the height, H, and base, B, of spikes 26 on the rails, and the spacing, S, between the spikes. The size and relative spacing between elements of stabilization device 8 may vary depending on patient and surgical requirements. In one example, first and second rails 14 and 16 may have a length, L, in a range from approximately 8.9 to approximately 12.7 centimeters. First rail 14 and second rail 16 may be the same or different lengths. In one example, the center-to-center width, W, between first and second rails 14 and 16 is in a range from approximately 7 to approximately 15 millimeters. Multiple spiked rail stabilization devices with varying rail-to-rail widths and/or rail lengths may be grouped together as a kit. In some cases, rails 14 and 16 may be fabricated in a standard size sufficiently long to accommodate the majority of patient anatomies and then cut to size during surgery. Each of rails 14 and 16 may include a thickness in a range from approximately 1 to approximately 5 millimeters. Rails 14 and 16 may be fabricated as circular or other shaped cylinders, e.g. rectangular or elliptical.

Spikes 26 are distributed along the length of first rail 14 and second rail 16. Each spike 26 may include a variety of tapered shapes, including, e.g. conical and pyramidal shapes. In some examples, different spikes 26 may have different shapes and/or sizes. In another example, spikes 26 may all have substantially the same shapes and/or sizes. In one example, each spike includes conical shape with a base diameter, B, of approximately 2 millimeters and a height, H, of approximately 2 millimeters. In one example, rails 14 and 16 are spaced and spikes 26 are sized such that when the rails clamp to the spine of a patient each spike is driven into a vertebra, e.g. into a spinous process of a vertebra approximately 1 millimeter. In other words, in this example, spikes 26 are driven into each vertebra by a distance of approximately 1 millimeter. Spikes 26 may be spaced evenly or unevenly along the length of rails 14 and 16.

The spacing, S, between successive spikes 26 may be configured such that, for a variety of patient anatomies, at least one spike will be arranged to engage each vertebra, e.g. each spinous process of each vertebra to which device 8 is intended to be connected to and stabilize. In one example, the spacing, S, between successive spikes 26 is approximately equal to 4 millimeters.

Spikes 26 may be fabricated as integral with rails 14 and 16. In other examples, spikes 26 may be individual components removably or non-removably attached to rails 14 and 16. For example, each spike 26 may include an externally-threaded post at the base of the spike that is configured to be received within an complementary internally-threaded aperture in one of rails 14 or 16.

Figure 3:
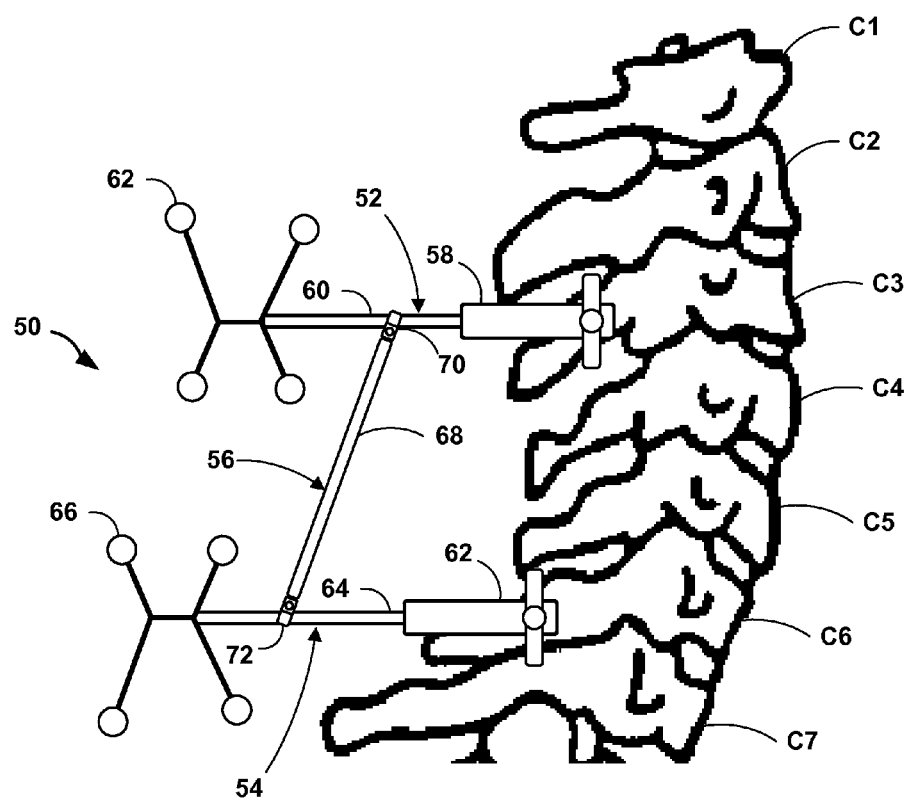
FIG. 3 is a schematic illustration of another example spinal stabilization device connecting two fiducial markers respectively attached to a cervical vertebra.

FIG. 3 is a schematic illustration of example tie-rod spinal stabilization device 50 arranged to be attached to cervical vertebrae, C1-C7, of spine 52. Tie-rod stabilization device 50 includes first fiducial marker 52, second fiducial marker 54, and tie-rod 56. First fiducial marker 52 includes clamp 58, shaft 60, and fiducial locators 62 extending from the end of shaft 60. Similarly, second fiducial marker 54 includes clamp 62, shaft 64, and fiducials 66 extending from shaft 64.

In FIG. 3, first fiducial marker 52 is connected to cervical vertebra C3 via clamp 58 and second fiducial marker 54 is connected to cervical vertebra C6 via clamp 62. In one example, clamp 58 and clamp 62 of first and second fiducial markers 52 and 54, respectively, may be substantially similar to clamp 12 described above with reference to the example of FIGS. 1A-2. Thus, in one example, clamp 58 and clamp 62 each include a c-clamp including a fixed jaw and an adjustable screw, which is driven by a handle. Shafts 60 and 64 of first and second fiducial markers 52 and 54, respectively, are connected to and extend from clamps 58 and 62, respectively. In another example, fiducial markers 52 and 54 may be connected to vertebrae by driving a shaft of the marker into the bone. For example, the shaft of a fiducial marker may include an externally threaded portion that is sized and shaped for being received within a correspondingly sized and shaped internally threaded mating receptacle of an externally-threaded self-tapping base.

Protruding from the end of shafts 60 and 64 are a number of fiducial locators 62 and 66, respectively, which are employed as part of a surgical navigation system to index the position of surgical instruments with respect to patient anatomy. Generally, fiducial locators 62 and 66 may include imageable substantially spherical structures that are locatable using a number of different imaging system modalities, including, e.g., optical motion capture, infrared (IR) motion capture, Magnetic Resonance (MR) or Computed Tomography (CT). In one example, fiducial locators 62 and 66 each include a sealed interior cavity, which may be filled with an imageable fluid that is visible on, e.g., an MRI or CT scan.

Tie-rod 56 includes rod 68 and first and second tie-rod clamps 70 and 72, respectively. First tie-rod clamp 70 is connected to one end of rod 68 and second tie-rod clamp 72 is connected to the other end. In the example of FIG. 3, tie-rod 56 is connected between shaft 60 and shaft 64 of first and second fiducial markers 52 and 54, respectively. In particular, first tie-rod clamp 70 is connected to shaft 60 of first fiducial marker 52 and second tie-rod clamp 72 is connected to shaft 64 of second fiducial marker 54. As will be described in detail with reference to FIG. 4, each of first and second tie-rod clamps 70 and 72 may include adjustable jaws that may be opened to at least partially surround shafts 60 and 64 and then closed to connect tie-rod 56 between first and second fiducial markers 52 and 54.

Tie-rod 56, including rod 68 and clamps 70 and 72, may be manufactured from a variety of materials, including metals such as steel and aluminum or various polymers. In some examples, tie-rod 56 is manufactured, in whole or in part, from a number of biocompatible materials that resist corrosion and degradation from bodily fluids including, e.g., titanium or stainless steel, or a biologically inert polymer.

Figure 4:
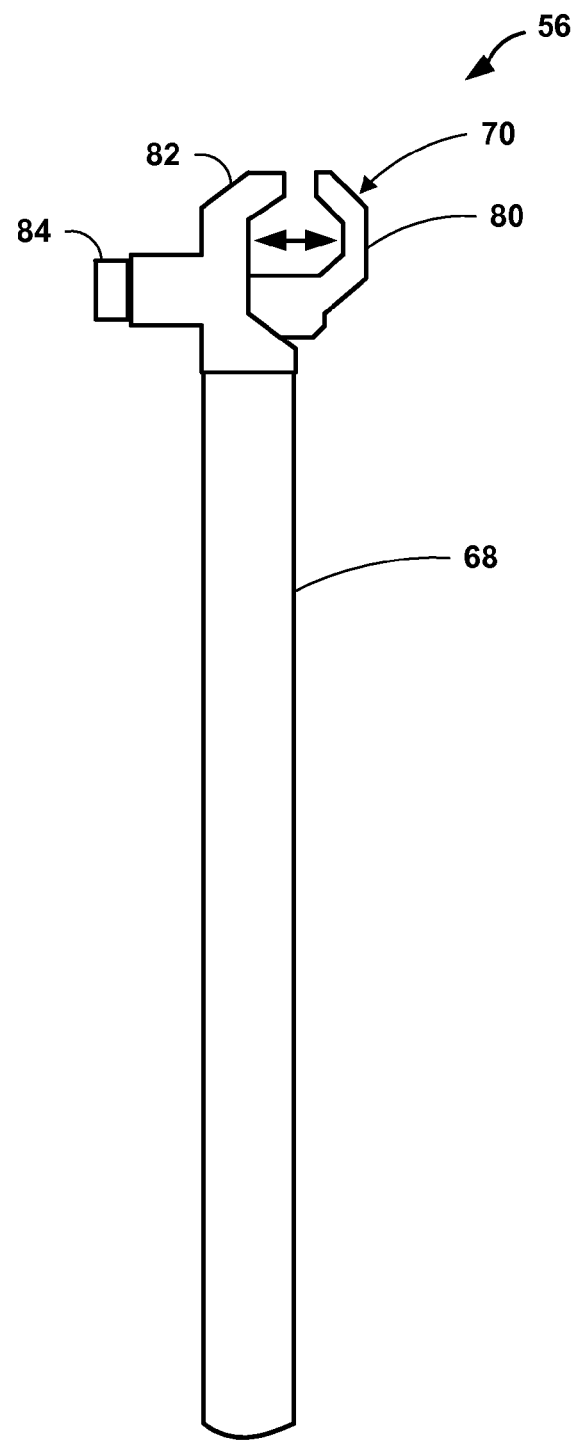
FIG. 4 is a broken view of an example tie-rod of the spinal stabilization device of FIG. 3.

FIG. 4 is a broken view of an example of tie-rod 56 of spinal stabilization device 50 of FIG. 3. In FIG. 4, tie-rod 56 includes rod 68 and first tie-rod clamp 70. Tie-rod clamp 70 includes fixed jaw 80, movable jaw 82, and set screw 84. In the example of FIG. 4, movable jaw 82 is configured to slide laterally to open and close clamp 70 by engaging set screw 84. Thus, clamp 70 may be adjusted by engaging set screw 84 to move jaw 82 away from fixed jaw 82 to open the clamp and position the clamp around a shaft of a fiducial marker, e.g. shaft 60 of first fiducial maker 52 from the example of FIG. 3. After positioning tie-rod clamp 70 around the shaft of the fiducial marker, set screw 84 may be engaged again to move jaw 82 toward fixed jaw 82 to close the clamp around the shaft, thereby connecting the end of rod 68 to the fiducial marker. Although not illustrated in the example of FIG. 4, clamp 70 may be configured to move relative to rod 68, e.g. by connecting the clamp to the rod via a single or multiple degree-of-freedom joint. For example, clamp 70 may be connected to rod 68 via a ball and socket joint configured to allow the clamp and rod to rotate in multiple directions relative to one another.

Referring again to tie-rod spinal stabilization device 50 of FIG. 3, connecting tie-rod 56 between first and second fiducial markers 52 and 54, respectively, aligns and fixes the vertebrae including and between the two vertebra to which the markers are connected. In the example of FIG. 3, connecting tie-rod 56 to fiducial markers 52 and 54 aligns and fixes cervical vertebrae C3-C6. However, in other examples, more or fewer vertebrae may be stabilized by a tie-rod stabilization device in accordance with this disclosure, such as device 50 of FIG. 3. The number of vertebra of a spine that are stabilized by a tie-rod spinal stabilization device according to this disclosure may be changed by attaching two fiducial markers to different vertebra at the endpoints of a desired stabilization zone and then connecting a tie-rod to the fiducial markers that spans the distance therebetween. In one example, the length of the tie-rod is adjustable, e.g., the tie-rod could have a telescoping shaft. In another example, a kit of tie-rod spinal stabilization devices may include tie-rods of multiple fixed lengths.

Various examples have been described. These and other examples are within the scope of the following claims.

The invention claimed is:

1. A spinal stabilization device comprising:
   a clamp configured to engage a vertebra of a spine;
   a first rail connected to the clamp and comprising a first plurality of spikes distributed longitudinally along the first rail; and
   a second rail extending from the clamp offset laterally from the first rail and comprising a second plurality of spikes distributed longitudinally along the second rail,
   wherein the first rail and the second rail are biased toward one another with the first plurality of spikes pointing toward the second plurality of spikes, and
   wherein the offset between the first rail and the second rail is in a range from approximately 7 to approximately 15 millimeters.

2. The device of claim 1, wherein at least one of the clamp, the first rail, and the second rail comprise at least one of a metal or a polymer.

3. The device of claim 1, wherein at least one of the clamp, the first rail, and the second rail comprise at least one of stainless steel, aluminum, or titanium.

4. The device of claim 1, wherein one or more of the first plurality of spikes or the second plurality of spikes comprises at least one of a conical or pyramidal shape.

5. The device of claim 1, wherein one or more of the first plurality of spikes or the second plurality of spikes comprises an externally-threaded post protruding from a base of the spike that is configured to be received within a complementary internally-threaded aperture in one of the first rail or the second rail, respectively.

6. The device of claim 1, wherein at least one of the first rail or the second rail comprises at least one of a circular, rectangular, or elliptical cylinder.

7. The device of claim 1, wherein at least one of the first rail or the second rail comprises a length in a range from approximately 8.9 to approximately 12.7 centimeters.

8. The device of claim 1, wherein at least one of the first rail or the second rail comprises a thickness in a range from approximately 1 to approximately 5 millimeters.

9. The device of claim 1, wherein one or more of the first plurality of spikes or the second plurality of spikes comprises a width at a base of the spike approximately equal to 2 millimeters.

10. The device of claim 1, wherein one or more of the first plurality of spikes or the second plurality of spikes comprises a height approximately equal to 2 millimeters.

11. The device of claim 1, wherein at least one of the first rail or the second rail comprises a material that requires a force in a range of approximately 50 to approximately 150 newtons to overcome an inherent bias of the first and second rails to increase the offset therebetween.

12. The device of claim 1, wherein the first and second rails each comprise a shape memory alloy which functions to bias the first and second rails to be offset from one another by a first distance at a first temperature and to be offset from one another by a second distance at a second temperature.

13. The device of claim 12, wherein the first temperature is less than the second temperature and the first distance is greater than the second distance.

14. The device of claim 12, wherein the shape memory alloy comprises a nickel-titanium alloy.

15. The device of claim 1, wherein the clamp comprises a C-clamp comprising a fixed jaw, an adjustable screw, and a handle configured to be engaged to adjust the screw.

16. A spinal stabilization device comprising:
    a clamp configured to engage a vertebra of a spine;
    a first rail connected to the clamp and comprising a first plurality of spikes distributed longitudinally along the first rail; and
    a second rail extending from the clamp offset laterally from the first rail and comprising a second plurality of spikes distributed longitudinally along the second rail,
    wherein the first rail and the second rail are biased toward one another with the first plurality of spikes pointing toward the second plurality of spikes, and
    wherein the clamp comprises a C-clamp comprising a fixed jaw, an adjustable screw, and a handle configured to be engaged to adjust the screw.

17. The device of claim 16, wherein at least one of the clamp, the first rail, and the second rail comprise at least one of a metal or a polymer.

18. The device of claim 16, wherein one or more of the first plurality of spikes or the second plurality of spikes comprises at least one of a conical or pyramidal shape.

19. The device of claim 16, wherein one or more of the first plurality of spikes or the second plurality of spikes comprises an externally-threaded post protruding from a base of the spike that is configured to be received within a complementary internally-threaded aperture in one of the first rail or the second rail, respectively.

20. The device of claim 16, wherein at least one of the first rail or the second rail comprises a length in a range from approximately 8.9 to approximately 12.7 centimeters.

21. The device of claim 16, wherein at least one of the first rail or the second rail comprises a thickness in a range from approximately 1 to approximately 5 millimeters.

22. The device of claim 16, wherein at least one of the first rail or the second rail comprises a material that requires a force in a range of approximately 50 to approximately 150 newtons to overcome an inherent bias of the first and second rails to increase the offset therebetween.

23. The device of claim 16, wherein the first and second rails each comprise a shape memory alloy which functions to bias the first and second rails to be offset from one another by a first distance at a first temperature and to be offset from one another by a second distance at a second temperature.

24. The device of claim 23, wherein the first temperature is less than the second temperature and the first distance is greater than the second distance.

25. A kit comprising:
    a plurality of spinal stabilization devices, each of which comprises:
        a clamp configured to engage a vertebra of a spine;
        a first rail connected to the clamp and comprising a first plurality of spikes distributed longitudinally along the first rail;
        a second rail extending from the clamp offset laterally from the first rail and comprising a second plurality of spikes distributed longitudinally along the second rail,
        wherein the first rail and the second rail are biased toward one another with the first plurality of spikes pointing toward the second plurality of spikes,
    wherein the plurality of spinal stabilization devices comprise a variety of offsets between the first rail and the second rail in a range from approximately 7 to approximately 15 millimeters.

26. The kit of claim 25, wherein the plurality of spinal stabilization devices comprise a plurality of first rails and a plurality of second rails, each of which pluralities of rails comprise a length in a range from approximately 8.9 to approximately 12.7 centimeters.

27. The kit of claim 25, wherein for each of the plurality of spinal stabilization devices, the clamp comprises a C-clamp comprising a fixed jaw, an adjustable screw, and a handle configured to be engaged to adjust the screw.

* * * * *